United States Patent [19]

Umemura et al.

[11] 4,278,614
[45] Jul. 14, 1981

[54] PROCESS FOR THE CATALYTICAL PREPARATION OF ACRYLONITRILE

[75] Inventors: Sumio Umemura; Kyoji Ohdan; Tokuo Matsuzaki; Hiroyuki Asada; Masao Tsuruoka, all of Ube, Japan

[73] Assignee: Ube Industries, Ltd., Ube, Japan

[21] Appl. No.: 74,232

[22] Filed: Sep. 10, 1979

[30] Foreign Application Priority Data

Sep. 13, 1978 [JP] Japan ................................ 53-111700

[51] Int. Cl.³ .......................................... C07C 120/14
[52] U.S. Cl. ................................ 260/465.3; 252/458; 252/469
[58] Field of Search ...................................... 260/465.3

[56] References Cited

U.S. PATENT DOCUMENTS

| | | | |
|---|---|---|---|
| 3,872,148 | 3/1975 | Umemura et al. | 260/465.3 |
| 3,895,049 | 7/1975 | Umemura et al. | 260/465.3 |
| 3,993,680 | 11/1976 | Grasselli et al. | 260/465.3 |
| 4,070,390 | 1/1978 | Umemura et al. | 260/465.3 |
| 4,097,518 | 6/1978 | Umemura et al. | 260/465.3 |

OTHER PUBLICATIONS

Abstract of Japanese Patent Applications Publications No. 45-35287, (1970) (Derwent).

Abstract of Japanese Patent Applications Publications No. 49-108018, (1974) (Derwent).

*Primary Examiner*—Joseph Paul Brust
*Attorney, Agent, or Firm*—Haseltine and Lake

[57] ABSTRACT

Acrylonitrile is produced from propylene in an excellent percent conversion of propylene, percent selectivity to acrylonitrile and percent yield of acrylonitrile, by bringing, at an elevated temperature, a reaction feed containing propylene, molecular oxygen and ammonia, each in gas phase, into contact with a catalyst consisting essentially of an oxide composition of the empirical formula:

$$Mo_aCo_bNi_cFe_dBi_eX_fTi_gO_h$$

wherein X represents at least one atom of an element selected from vanadium and tellurium; the subscripts a, b, c, d, e, f and g respectively denote the numbers of the respective atoms of the elements, the ratio a:b:c:d:e:f:g being in the range of 10:0 to 10:0 to 10:1 to 7:0.08 to 1.1:0.01 to 1:1 to 15, and the ratio of a to the sum of b and c being in a range of 10:3 to 10, and; the subscript h represents the number of oxygen atoms which satisfies the average valency of the elements, the ratio a:h being in a range of 10:36.7 to 84.1.

16 Claims, No Drawings

PROCESS FOR THE CATALYTICAL PREPARATION OF ACRYLONITRILE

FIELD OF THE INVENTION

The present invention relates to a process for the catalytical preparation of acrylonitrile. More particularly, the present invention relates to a process for the production of acrylonitrile at a high percent of yield and at a space time yield thereof by means of a catalytical ammoxidation of propylene, while maintaining the undersirable production of by-products, especially, acrolein, at a very low level.

BACKGROUND OF THE INVENTION

It is known that acrylonitrile can be produced from propylene in various processes in which propylene is brought into contact with molecular oxygen and ammonia in a gas phase in the presence of a catalyst at an elevated temperature. These processes are known as catalytical ammoxidation processes for propylene. This ammoxidation of propylene can be effected only in the presence of a catalyst. U.S. Pat. No. 2,904,580 disclosed, for the first time, a P-Mo-Bi-O type catalyst effective for the ammoxidation of propylene. After this U.S. patent, various types of catalysts were provided for the ammoxidation process for propylene. For example, U.S. Pat. Nos. 3,226,422, 3,254,110, 3,641,102 and 3,746,656 and Japanese Patent Application Publication (KOKOKU) No. 45-35287(1970), respectively, disclosed an Fe-Bi-Mo-P-O type, an Fe-Ni-Mo-P-O an Fe-Bi-Mo-P-O type, an Fe-Ni-Mo-P-O type, a Te-Mo-Fe-O type, a Tl-P-Mo-Fe-Bi-Mg,Co and/or Ni-O type and a P-Mo-Bi-Ni-,Co,Zn and/or Sn-O type catalyst, each of which is effective for the process of producing acrylonitrile from propylene. Also, Japanese Patent Application Laying-open (KOKAI) No. 49-108018(1974) disclosed a Co-Fe-Bi-W-Mo-Si-Tl, alkali metal and/or alkaline earth metal-O type catalyst useful for the ammoxidation process for propylene.

However, when the above-mentioned types of conventional catalysts are used in the process for producing acrylonitrile by the ammoxidation of propylene, the following disadvantages are exhibited.

1. The catalytical ammoxidation reaction temperature at which acrylonitrile can be produced at the highest yield is about 450° C., which is undesirably high. This undesirably high reaction causes the durability in catalytic activity of the catalyst to be shortened and undesirable side-reactions to be promoted.

2. The reaction time (contact time) necessary for producing acrylonitrile at a high yield is undesirably long. The undesirably long reaction time results in the same disadvantages as those of the undesirably high reaction temperature.

3. The space time yield of acrylonitrile is undesirably low. This undesirably low space time yield of acrylonitrile causes the catalyst to be consumed in a large amount and the production cost of acrylonitrile to be high.

Also, when the above-mentioned conventional catalyst is used to convert propylene into acrylonitrile under a certain reaction condition which is effective for carrying out the reaction at a high percent conversion of propylene, sometimes such a reaction condition causes the reaction to exhibit a reduced percent of selectivity to acrylonitrile and a poor percent of yield of acrylonitrile, even if the catalyst is effective for producing acrylonitrile at a high percent selectivity thereto under another reaction condition.

Some of the conventional catalysts containing molybdenum, bismuth, iron and cobalt and/or nickel are effective for producing acrylonitrile at a high percent of yield thereof.

However, some of the bismuth-containing catalysts exhibit a disadvantage in that the necessary reaction temperature is undesirably high, the necessary reaction time is undesirably long, and the space time yield of acrylonitrile is undesirably low. Accordingly, it is desired to modify the conventional bismuth-containing catalysts so as to make possible the production of acrylonitrile from propylene at a high percent of conversion of propylene, at a high percent of selectivity and a high percent of yield of acrylonitrile, at a high space time yield of acrylonitrile, at a relatively low reaction temperature during a relatively short reaction time and at a low cost.

U.S. Pat. No. 4,070,390, having the same inventors as of the present invention, disclosed a new Mo-Bi-Fe-Co-V and/or Te-O type catalyst effective for producing acrylonitrile from propylene. This catalyst contains bismuth in a very small amount of from 0.01 to 0.7 atoms per atom of molybdenum. However, this catalyst is capable of ammoxidizing propylene within a short reaction time of about 1.7 seconds, at a low reaction temperature of about 400° C., at a high percent of conversion of propylene and at a high percent of selectivity to acrylonitrile. Therefore, this catalyst can produce acrylonitrile at a high yield of 80% or more, at a high space time yield of 250 g/l of catalyst.hour or more. It has been found, however, that this catalyst exhibits such a disadvantage that the reaction product contains a relatively large amount, about 3% by weight, of acrolein as a by-product. This acrolein causes some difficulties in the refining process of the reaction product. That is, acrolein is easily polymerized in the reaction product and the polymerized acrolein adheres onto the inside surface of the reaction equipment. Also acrolein easily reacts with hydrocyanic acid, which is contained as a by-product in the reaction product, and which is useful as a material for producing acetocyanohydrin, to produce acrolein cyanohydrin. Accordingly, it is difficult to recover the hydrocyanic acid from the reaction product. Furthermore, the reaction product contains acrylic acid as a by-product. The acrylic acid is readily polymerized and the resultant polymer undesirably deposits on the inside surface of the reaction equipment. Also, the catalyst of U.S. Pat. No. 4,070,390 exhibits such a disadvantage that, even if the catalyst is shaped into tablets by using a tablet-forming machine, the resultant tablets exhibit a poor crushing strength. Accordingly, when used in a practical process, the tablets of the catalyst are readily deteriorated, divided into fine particles and/or worn down.

British Pat. No. 1,436,475, having the same inventors as the present invention, disclosed a Mo-Bi-Fe-Co-W-Ca-Ti-O type catalyst useful for the production of acrylonitrile from propylene. This catalyst can be shaped into tablets having an excellent crushing strength. The composition of this catalyst is effective for preventing the loss of molybdenum from the catalyst and the deterioration, crushing and/or wearing of the catalyst during reaction. Also, the catalyst is effective for producing acrylonitrile at a high yield thereof. However, the catalyst exhibits such disadvantages that the reaction product contains a relatively large amount of acrolein as a by-product, that the necessary reaction time is undesirably long, that is, about 3 seconds and that the space time yield of acrylonitrile is unsatisfactorily low.

SUMMARY OF THE INVENTION

An object of the present invention is to provide a process for the catalytical preparation of acrylonitrile by using a catalyst containing a small amount of bismuth, which catalyst is capable of producing acrylonitrile at in a high percent yield and space time yield thereof, even at a low reaction temperature of about 400° C. and during a short reaction time of about 1.7 seconds.

Another object of the present invention is to provide a process for the catalytical preparation of acrylonitrile by using a catalyst which is effective for increasing percent selectivity to acrylonitrile and decreasing the yield of undesirable acrolein.

Still another object of the present invention is to provide a process for the catalytical preparation of acrylonitrile by using a catalyst which is capable of being shaped into tablets having a high crushing strength.

The above-mentioned objects can be attained by the process of the present invention, which comprises bringing, at an elevated temperature, a reaction feed containing propylene, molecular oxygen and ammonia, each in gas phase, into contact with a catalyst consisting essentially of an oxide composition of the empirical formula:

$$Mo_aCo_bNi_cFe_dBi_eX_fTi_gO_h$$

wherein X represents at least one atom of an element selected from vanadium and tellurium; the subscripts a, b, c, d, e, f and g respectively denote the numbers of the respective atoms of the elements, the ratio a:b:c:d:e:f:g being in the range of 10:0 to 10:0 to 10:1 to 7:0.08 to 1.1:0.01 to 1:1 to 15, and the ratio of a to the sum of b and c being in a range of 10:3 to 10, and; the subscript h represents the number of oxygen atoms which satisfies the average valency of the elements, the ratio a:h being in a range of 10:36.7 to 84.1.

The process of the present invention is characterized by using the new type of catalyst as specified above. This catalyst is characterized by containing titanium together with vanadium and/or tellurium, in addition to the oxide composition, Mo-Co-Ni-Fe-Bi-O. This catalyst allows the process of the present invention to exhibit not only the following advantages (1) through (4), but, also, the advantages (5) and (6).

(1) It is possible to produce acrylonitrile from propylene at a high percent conversion of propylene, at a high percent selectivity to acrylonitrile and at a high yield of 80% or more of acrylonitrile, even at a relatively low reaction temperature of about 400° C. and even during a relatively short reaction time of about 1.7 seconds.

(2) The consumption of the catalyst is small and the cost of the reaction equipment is low, because the space time yield of acrylonitrile in the process of the present invention is high, that is, 250 g/l of catalyst.hour or more.

(3) The durability in activity of the catalyst is high and undesirable side reactions are significantly restricted because the reaction temperature is relatively low.

(4) The yield of the undesirable acrolein is very low, that is, about one half that in the conventional processes.

(5) The catalyst can be shaped into tablets which exhibit a high crushing strength.

It is especially important that the catalyst usable for the process of the present invention can reduce the yield of the undesirable acrolein. Therefore, the hydrocyanic acid, which is valuable as a material for producing acetocyanohydrin, can be easily recovered from the reaction product. This advantage of the catalyst usable for the process of the present invention cannot be anticipated from either the conventional Mo-Bi-Fe-Co-V and/or Te-O type catalyst or the conventional Mo-Bi-Fe-Co-W-Ca-Ti-O type catalyst. Also, it is important that the catalyst usable for the process of the present invention exhibit all of the same advantages as those of the conventional Mo-Bi-Fe-Co-V and/or Te-O and Mo-Bi-Fe-Co-W-Ca-Ti-O type catalysts.

DETAILED DESCRIPTION OF THE INVENTION

In the process of the present invention, a reaction feed containing propylene, molecular oxygen and ammonia, each in gas phase, is brought into contact with a catalyst at an elevated temperature. The catalyst consists essentially of an oxide composition of the empirical formula:

$$Mo_aCo_bNi_cFe_dBi_eX_fTi_gO_h$$

wherein X represents at least one atom of an element selected from vanadium and tellurium; the subscripts a, b, c, d, e, f and g respectively denote the numbers of the respective atoms of molybdenum, cobalt, nickel, iron, bismuth, the element X and titanium, and; the subscript h represents the number of oxygen atoms which satisfies the average valency of the elements. The ratio a:b:c:d:e:f:g is in a range of 10:0 to 10:0 to 10:1 to 7:0.08 to 1.1:0.01 to 1:1 to 15, preferably, 10:1 to 7:0 to 7:1.5 to 7:0.1 to 0.5:0.05 to 0.5:2 to 10, and the ratio of a to the sum of b and c (a:(b+c)) is in a range of 10:3 to 10, preferably, 10:4 to 9. Also, the ratio a:h is in a range of from 10:36.7 to 84.1. It is important that all of the above-mentioned ratios be within the respective ranges specified above. If any one of the above-mentioned ratios falls outside of the corresponding range, the resultant catalyst causes the ammoxidation reaction of propylene to exhibit a poor percent conversion of propylene, a poor percent selectivity to acrylonitrile, a poor space time yield of acrylonitrile and/or a poor percent yield of acrylonitrile.

Especially, it is most important that the catalyst used for the present invention contains, in addition to the Mo-Co-Ni-Fe-Bi-V and/or Te, titanium in an amount of from 1 to 15 atoms per 10 atoms of molybdenum. If the amount of titanium in the catalyst is less than 1 atom per 10 atoms of molybdenum, the resultant catalyst will not be able to reduce the yield of the undesirable acrolein and cannot be shaped into tablets having a high crushing strength. That is, in this case, the resultant cataylst will exhibit the same disadvantages as those of the conventional Mo-Bi-Fe-Co-V and/or Te-O type catalyst of U.S. Pat. No. 4,070,390. Also, if the amount of titanium in the catalyst is more than 15 atoms per 10 atoms of molybdenum, the resultant catalyst will cause the ammoxidation reaction of propylene to exhibit a poor percent conversion of propylene and a poor percent selectivity to acrylonitrile. Generally, the increase in the content of titanium in the catalyst causes the yield of the undesirable acrolein to be reduced. However, the increase in the content of titanium over the level of 15 atoms per 10 atoms of molybdenum is not effective for reducing the yield of acrolein. The respective elements in the catalyst usable for the process of the present invention exist in the form of oxides thereof. Some of the oxides may form a complex and a plurality of the elements may form a compound together with oxygen.

The catalyst usable for the process of the present invention can be prepared by any conventional method pertinent for producing a conventional oxide catalyst. Usually, the catalyst can be prepared by providing an aqueous mixture containing the respective element-containing compounds, that is, a molybdenum-containing compound, a cobalt-containing compound, a nickel-containing compound, an iron-containing compound, a bismuth-containing compound, at least one member selected from vanadium- and tellurium-containing compounds and a titanium-containing compound, together with water, by converting the aqueous mixture into a dried solid mixture and by calcining the dried solid mixture at a temperature of from 500° to 700° C., preferably from 530° to 670° C. The respective element-containing compound may be in the form of salts, acid, hydroxides or oxides. In the preparation of the catalyst, the dried solid mixture of the respective element-containing compounds may be prepared in such a manner than predetermined amounts of the respective element-containing compounds, for example, salts, hydroxide or oxides, are mixed all together in water to provide an aqueous paste and, then, the aqueous paste is dried, or; that predetermined amounts of the respective element-containing compounds are dissolved and/or suspended in water, and then, the aqueous solution, suspension or solution-suspension mixture are subjected to an evaporation process, so as to remove water therefrom, or; that an aqueous solution of the respective element-containing water-soluble compounds is prepared, the respective elements are co-precipitated in the form of water-insoluble compounds, and, then, the co-precipitates are dried.

The calcining operation of the dried solid mixture is carried out for 0.5 to 20 hours, preferably, 2 to 15 hours. If the calcining temperature is lower than 500° C., sometimes the use of the resultant catalyst causes the percent selectivity to acrylonitrile to be poor. Also, if the calcining temperature is higher than 700° C., sometimes the use of the resultant catalyst causes the percent conversion of propylene to be poor. Accordingly, it is preferable that the calcining temperature be in the range of from 500° to 700° C., more preferably, from 530° to 670° C.

The molybdenum-containing compound may be selected from molybdic acid, ammonium molybdate, molybdenum trioxide, phosphomolybdic acid, ammonium phosphomolybdate and molybdenum sulfide.

The cobalt-containing compound may be selected from cobalt nitrate, cobalt carbonate, cobalt chloride, cobalt (II) oxide, cobalt (III) oxide, tricobalt tetraoxide, cobalt (II) hydroxide, cobalt (III) hydroxide, cobalt hydroxycarbonate, cobalt oxalate and cobalt sulfide.

The nickel-containing compound may be selected from nickel nitrate, nickel carbonate, nickel oxide, nickel oxalete, nickel hydroxide, nickel chloride, nickel acetate and nickel sulfide.

The iron-containing compound may be selected from ferrous nitrate, ferric nitrate, ferrous oxide, ferric oxide, iron sulfides, ferrous chloride, ferric chloride, ferrous carbonate, ferric carbonate, ferrous hydroxide, ferric hydroxide, ferrous sulfate and ferric sulfate.

The bismuth-containing compound may be selected from bismuth nitrate, bismuth chloride, bismuth oxide, bismuth hydroxide, bismuth hydroxynitrate, bismuth oxycarbonate, bismuth oxynitrate and bismuth oxychloride.

The vanadium-containing compound may be selected from ammonium metavanadate, meta-vanadic acid, vanadyl oxalate, vanadium tetrachloride, vanadium pentaoxide, vanadium oxychloride and vanadyl chloride.

The tellurium-containing compound may be selected from ortho-telluric acid, meta-telluric acid, tellurium dioxide, tellurium chloride, tellurium oxalate and tellurium nitrate.

The titanium-containing compound may be selected from titanic acid, anatose type titanium dioxide, rutile type titanium dioxide, titanium chloride, titanium sulfate and titanium oxynitrate.

Compounds containing two or more metallic elements selected from, molybdenum, cobalt, nickel, iron, bismuth, vanadium, tellurium and titanium, for example, cobalt molybdate, iron molybdate, bismuth titanate, may be used for the preparation of the catalyst. The following is an example of the preparation of the catalyst usable for the present invention and containing an oxide composition of molybdenum, cobalt, nickel, iron, bismuth, tellurium and titanium.

A necessary amount of a water-soluble molybdenum-containing compound, for example, molybdic acid or ammonium molybdate, is dissolved in hot water at a temperature of from 50° to 90° C. Necessary amounts of tellurium dioxide and titanium dioxide are suspended in the aqueous solution of the molybdenum-containing compound, while stirring the aqueous solution-suspension. Next, an aqueous solution of necessary amounts of a water-soluble cobalt compound, for example, cobalt nitrate or cobalt chloride, a water-soluble nickel compound, for example, nickel nitrate or nickel acetate, and a water-soluble iron compound, for example, ferrous nitrate or ferric nitrate, and a separate aqueous nitric acid solution of a nitric acid-soluble bismuth compound, for example, bismuth nitrate or bismuth hydroxide, are added dropwise to the above-prepared aqueous solution-suspension, while stirring the mixture, to provide an aqueous slurry. The aqueous slurry is subjected to evaporation to provide a dried solid mixture. The dried solid mixture is calcined in air atmosphere at a temperature of from 500° to 700° C. for 0.5 to 20 hours, preferably, at a temperature of from 530° to 670° C. for 2 to 15 hours. After the calcining operation, a desired catalyst is obtained.

The titanium dioxide and tellurium dioxide, which are insoluble in water, may be added into the aqueous solution which has been prepared by adding dropwise the aqueous solution of the water-soluble cobalt, nickel and iron compound, and the aqueous nitric acid solution of the nitric acid-soluble bismuth compound, into the aqueous solution of the water-soluble molybdenum compound.

In the preparation of the catalyst, it is preferable to use water-soluble compounds of the respective elements. This is effective for uniformly mixing the respective element-containing compounds with each other and for preventing variations in quality and composition of the resultant catalyst.

The catalyst usable for the present invention may be used alone. Otherwise, the catalyst may be borne on a carrier. The carrier may be selected from any of the conventional ones which are usable for the catalyst for the ammoxidation process of propylene, for example, silica in the form of gel or sol, alumina, silica-alumina, zirconia, titania, diatomaceous earth and silicates. There is no limitation to the amount of the carrier to be used to support the catalyst. Usually, it is preferable that the carrier be used in an amount of 0.05 to 3 g, more preferably, 0.1 to 2 g, per g of the catalyst.

The size and shape of the catalyst are not limited to a special size and shape. That is, the catalyst can be screened into a desired size and can be formed into a desired form, for example, powder, grains, pellets or tablets having a desired rigidity, depending upon the purpose and conditions under which the catalyst is used.

The process of the present invention can be effected by using any type of reaction bed selected from fixed beds, moving beds and fluidized beds. In the case where a fluidized reaction bed is used, it is preferable that, in the preparation of the catalyst, the catalyst be added to a carrier such as silica sol, and the mixture be spray-dried to form catalyst particles each having a size of from 20 to 100 microns.

In the process of the present invention, the reaction feed can be prepared by mixing a propylene source in gas phase with ammonia and a molecular oxygen-containing gas. It is preferable that the reaction feed contains, in addition to propylene, ammonia and molecular oxygen, an inert diluent gas which does not substantially affect the ammoxidation reaction of propylene. The inert diluent gas may be selected from steam, nitrogen gas and carbon dioxide gas. The steam is effective for increasing the percent selectivity to acrylonitrile and for enhancing the durability in catalytic activity of the catalyst. Accordingly, in the case where the process of the present invention is carried out by using a fixed reaction bed, it is preferable to add the steam to the reaction feed. In this case, the steam is used in an amount of from 0.1 to 5 moles, preferably, from 0.5 to 4 moles, per mole of propylene. However, in the case where a fluidized bed is used in the process of the present invention, the reaction produces water as a by-product and the water in the form of vapor is contained in the reaction mixture. In this case, the mixed water vapor exhibits the above-mentioned advantages of steam. Therefore, the ammoxidation reaction on the fluidized bed can be smoothly effected even without adding steam to the reaction feed.

The process of the present invention can be smoothly carried out under the same conditions as those common in the conventional ammoxidation processes. That is, the reaction feed may come into contact with the catalyst under ambient atmospheric pressure, slightly increased pressure or reduced pressure.

In the process of the present invention, the contact of the reaction feed with the catalyst is carried out preferably at a temperature of from 330° to 470° C., more preferably, from 350° to 450° C., still more preferably, at about 400° C., for period of from 0.2 to 7 seconds, more preferably, from 0.5 to 4 seconds, still more preferably, about 1.7 seconds.

The propylene source to be used in the process of the present invention is not required to have propylene of a high purity. The propylene source may contain a small amount of inert lower hydrocarbons, for example, methane, ethane and propane, as long as the hydrocarbons do not affect the ammoxidation of propylene. The amount of the inert hydrocarbons in the propylene source is preferably limited to a level of 0.5 moles or less, more preferably, 0.1 mole or less, per mole of propylene. Also, it is preferable that the propylene source be free from reactive hydrocarbons, for example, n-butylene and acetylene, which affect the ammoxidation of propylene.

The molecular oxygen-containing gas may be a pure or industrially pure oxygen gas. However, the molecular oxygen-containing gas is not required to have a high degree of concentration of oxygen. Generally, air is used as a molecular oxygen-containing gas because of the economical advantage.

In a preferable embodiment of the reaction feed, the molecular oxygen is used in an amount of from 1 to 4 moles, more preferably, from 1.2 to 3 moles, per mole of propylene, and the ammonia is used in an amount of from 0.5 to 2 moles, more preferably, from 0.8 to 1.2 moles per mole of propylene.

Also, the reaction feed preferably contains propylene in a concentration of from 1 to 20%, more preferably, from 2 to 10%, by volume.

After completing the ammoxidation of propylene, the resultant acrylonitrile can be isolated from the reaction mixture by any isolating methods, for example, the methods disclosed in U.S. Pat. Nos. 3,424,781 and 3,688,002.

The specific examples set forth below will serve to more fully explain the practice of the process of the present invention. However, it should be understood that the examples are only illustrative and should be in no way limit the scope of the present invention.

In the examples, the percent of conversion of propylene, percent of selectivity to acrylonitrile, percent of yield of acrylonitrile, percent of yield of acrolein and space time yield of acrylonitrile were respectively calculated in accordance with the following equations.

Percent of conversion of propylene $= (X_1 - X_2)/X_1 \times 100$

Percent of selectivity to acrylonitrile $= Y/(X_1 - X_2) \times 100$

Percent of yield of acrylonitrile $= (Y/X_1) \times 100$

Percent of yield of acrolein $= (A/X_1) \times 100$ and

Space time yield of acrylonitrile (g/l of catalyst·hr) $(A/X_1) \times 100$ wherein:

$X_1$: a molar amount of propylene contained in the reaction feed prior to the start of the reaction;

$X_2$: a molar amount of propylene contained in the reaction mixture after the completion of the reaction;

Y: a molar amount of the resultant acrylonitrile;

A: a molar amount of the resultant acrolein;

W: an amount in gram of the resultant acrylonitrile produced in one hour, and;

Z: an amount in liter of a catalyst used.

EXAMPLES 1 THROUGH 15

In Exampel 1, a solution was prepared by dissolving 166.1 g of ammonium molybdate tetrahydrate $[(NH_4)_6Mo_7O_{24}.4H_2O]$ in 200 ml of hot water at a temperature of 80° C. 1.5 g of tellurium dioxide $[TeO_2]$ and 37.6 g of titanium dioxide $[TiO_2]$ were suspended in the above-prepared solution while stirring it, to provide an aqueous solution-suspension. Separately, an aqueous solution which had been prepared by dissolving 136.9 g of cobalt nitrate [Co(NO$_3$)$_2$.6H$_2$O], 54.8 g of nickel nitrate [Ni(NO$_3$)$_2$.6H$_2$O] and 76.1 g of ferric nitrate [Fe(NO$_3$)$_3$.9H$_2$O] in 250 ml of hot water at a temperature of 80° C., and a solution of 9.12 g of bismuth nitrate [Bi(NO$_3$)$_3$.5H$_2$O] in 10 ml of a 15% nitric acid aqueous solution, were added dropwise to the aqueous solution-suspension to provide a slurry mixture.

The slurry mixture was dried at a temperature of 130° C. while stirring it, to convert it into a dried solid mixture. The resultant solid mixture was reduced to powder, and the powder was shaped into tablets, each having a diameter of 5 mm and a thickness of 5 mm, by using a tablet forming machine. The tablets were calcined at a temperature of 550° C., in the atmosphereic air, for 5 hours. The resultant catalyst exhibited an atomic ratio of the elements as shown in Table 1.

The tablets were subjected to measurement of the crushing strength thereof. The measurement was carried out by placing pressing a tablet between a pair of plates. The pressure was increased until the tablet was broken. The crushing strength of the tested tablet is expressed by the pressure under which the tablet is broken. The measurement was repeated for 50 tablets and the crushing strength of the catalyst was expressed by an average value of the crushing strengths of the 50 tablets.

The catalyst of the present example exhibited a crushing strength of 7.4 kg/tablet.

8 ml of the above-prepared catalyst tablets were placed in a U-shaped glass reaction tube having an inside diameter of 8 mm. A reaction feed containing propylene, ammonia, air and steam in a molar ratio of 1:1:11:2 was passed through the reaction tube at a flow rate of 282 ml/min, a temperature of 400° C. and under ambient pressure. The contact time was 1.7 seconds.

The above-mentioned reaction operation was continued for 2 hours. As a result of the reaction, acrylonitrile was obtained at a high percent conversion of propylene of 97.4%, at a high percent selectivity to acrylonitrile of 85.7%, at a high percent yield of acrylonitrile of 83.5% and at a high space time yield of acrylonitrile of 279 g/l of catalyst hour. The percent yield of acrolein was very small, that is, 0.7%.

In each of Examples 2 through 15, the same procedures as those described in Example 1 were carried out, except that the atomic ratio of the elements in the resultant catalyst was as indicated in Table 1. The results of each example are shown in Table 1.

TABLE 1

| Example No. | Atomic ratio of elements in catalyst | | | | | | Percent of conversion of propylene | Percent of selectivity to acrylonitrile | Percent of yield of acrylonitrile | Percent of yield of acrolein |
|---|---|---|---|---|---|---|---|---|---|---|
| | Mo | Co | Ni | Fe | Bi | Te | Ti | | | | |
| 1 | 10 | 5 | 2 | 2 | 0.2 | 0.1 | 5 | 97.4 | 85.7 | 83.5 | 0.7 |
| 2 | 10 | 5 | 2 | 2 | 0.2 | 0.1 | 1 | 98.0 | 82.9 | 81.3 | 1.0 |
| 3 | 10 | 5 | 2 | 2 | 0.2 | 0.1 | 3 | 97.8 | 85.1 | 83.2 | 0.8 |
| 4 | 10 | 5 | 2 | 2 | 0.2 | 0.1 | 7 | 97.2 | 85.2 | 82.8 | 0.6 |
| 5 | 10 | 5 | 2 | 2 | 0.2 | 0.1 | 10 | 95.7 | 85.0 | 81.3 | 0.6 |
| 6 | 10 | 5 | 2 | 2 | 0.2 | 0.1 | 15 | 93.5 | 85.0 | 79.5 | 0.5 |
| 7 | 10 | 4 | 3 | 2 | 0.2 | 0.1 | 5 | 97.2 | 85.4 | 83.0 | 0.8 |
| 8 | 10 | 2 | 5 | 2 | 0.2 | 0.1 | 5 | 96.5 | 84.7 | 81.8 | 0.8 |
| 9 | 10 | 4 | 2 | 2 | 0.2 | 0.1 | 5 | 97.1 | 84.4 | 82.0 | 0.7 |
| 10 | 10 | 6 | 3 | 2 | 0.2 | 0.1 | 5 | 98.8 | 82.3 | 81.3 | 0.8 |
| 11 | 10 | 7 | 0 | 2 | 0.2 | 0.1 | 5 | 97.0 | 84.6 | 82.1 | 0.7 |
| 12 | 10 | 0 | 7 | 2 | 0.2 | 0.1 | 5 | 95.3 | 83.3 | 79.4 | 0.8 |
| 13 | 10 | 5 | 2 | 2 | 0.1 | 0.1 | 5 | 97.0 | 85.1 | 82.5 | 0.7 |
| 14 | 10 | 5 | 2 | 3 | 0.2 | 0.1 | 5 | 97.1 | 85.9 | 83.4 | 0.7 |
| 15 | 10 | 5 | 2 | 2 | 0.2 | 0.3 | 5 | 98.5 | 84.0 | 82.7 | 0.7 |

COMPARISON EXAMPLES 1 THROUGH 7

In each of Comparison Examples 1 through 7, the same procedures as those mentioned in Example 1 were carried out, except that the resultant catalyst exhibited an atomic ratio of the elements therein as shown in Table 2. The results of each comparison example are shown in Table 2.

TABLE 2

| Comparison Example No. | Atomic ratio of elements in catalyst | | | | | | | Percent of conversion of propylene | Percent of selectivity to acrylonitrile | Percent of yield of acrylonitrile | Percent of yield of acrolein |
|---|---|---|---|---|---|---|---|---|---|---|---|
| | Mo | Co | Ni | Fe | Bi | Te | Ti | | | | |
| 1 | 10 | 5 | 2 | 2 | 0.2 | 0.1 | 0 | 97.2 | 82.7 | 80.4 | 3.8 |
| 2 | 10 | 5 | 2 | 2 | 0.2 | 0.1 | 20 | 84.3 | 84.5 | 71.2 | 0.5 |
| 3 | 10 | 1 | 1 | 2 | 0.2 | 0.1 | 5 | 68.5 | 78.5 | 53.8 | 0.5 |
| 4 | 10 | 5 | 2 | 2 | 0.2 | 0 | 5 | 86.1 | 80.1 | 69.0 | 0.6 |
| 5 | 10 | 10 | 4 | 4 | 0.4 | 0.2 | 10 | 72.6 | 70.5 | 51.2 | 1.1 |
| 6 | 10 | 5 | 2 | 2 | 1.5 | 0.1 | 5 | 83.8 | 81.0 | 67.9 | 0.8 |
| 7 | 10 | 5 | 2 | 2 | 0.2 | 2 | 5 | 99.0 | 55.3 | 54.7 | 0.6 |

EXAMPLES 16 THROUGH 20 AND COMPARISON EXAMPLE 8 THROUGH 10

In each of Examples 16 through 18, the same procedures as those described in Example 1 were carried out, except that the tellurium dioxide was replaced with ammonium metavanadate and the resultant catalyst had an atomic ratio of the elements as indicated in Table 3.

In Example 19, the same procedures as those described in Example 1 were carried out, except that ammonium metavanadate was used in addition to the tellurium dioxide and the resultant catalyst had an atomic ratio of the elemens as shown in Table 3.

In Example 20, the same procedures as those described in Example 1 were carried out, except that 143 ml of an aqueous sol containing 30% by weight of silica was added to the slurry mixture, the resultant catalyst was borne by a silica carrier in an amount of 20% by weight, and the catalyst had an atomic ratio of the elements as indicated in Table 3.

In comparison Examples 8 through 10, the same procedures as those mentioned in Example 1 were carried out, except that the tellurium dioxide was replaced with ammonium metavanadate and the resultant catalyst exhibited an atomic ratio of the elements as indicated in Table 3.

The results of the Examples 16 through 20 and Comparison Examples 8 through 10 are also shown in Table 3.

TABLE 3

| Example No. | Atomic ratio of elements in catalyst | | | | | | | Percent of conversion of propylene | Percent of selectivity to acrylonitrile | Percent of yield of acrylonitrile | Percent of yield of acrolein |
|---|---|---|---|---|---|---|---|---|---|---|---|
| | Mo | Co | Ni | Fe | Bi | V | Te | Ti | | | | |
| Example 16 | 10 | 5 | 2 | 2 | 0.2 | 0.5 | 0 | 5 | 98.8 | 82.0 | 81.0 | 0.7 |
| 17 | 10 | 5 | 2 | 2 | 0.2 | 0.1 | 0 | 2 | 98.2 | 83.5 | 82.0 | 0.9 |
| 18 | 10 | 5 | 2 | 2 | 0.2 | 0.1 | 0 | 7 | 97.5 | 84.8 | 82.7 | 0.6 |
| 19 | 10 | 5 | 2 | 2 | 0.2 | 0.1 | 0.1 | 5 | 97.8 | 85.0 | 83.1 | 0.7 |
| 20 | 10 | 5 | 2 | 2 | 0.2 | 0 | 0.1 | 5 | 97.7 | 85.7 | 83.7 | 0.6 |
| Comparison Example 8 | 10 | 5 | 2 | 2 | 0.2 | 0.1 | 0 | 0 | 98.0 | 81.5 | 79.9 | 3.7 |
| 9 | 10 | 5 | 2 | 2 | 0.2 | 0.1 | 0 | 20 | 84.8 | 84.0 | 71.2 | 0.5 |
| 10 | 10 | 1 | 1 | 2 | 0.2 | 0.1 | 0 | 5 | 70.2 | 77.2 | 54.0 | 0.6 |

EXAMPLE 21

The same reaction as that mentioned in Example 1 was continuously carried out for 500 hours by using the same catalyst ($Mo_{10}Co_5Ni_2Fe_2Bi_{0.2}Te_{0.1}Ti_5$) as that mentioned in Example 1. No deterioration in the catalytic activity of the catalyst was observed. After the completion of the 500 hours reaction, it was found that the percent of conversion of propylene was 97.8%, the percent of selectivity to acrylonitrile was 85.9%, the percent of yield of acrylonitrile was 84.0% and the percent of yield of acrolein was 0.6%.

What we claim is:

1. A process for the catalytical preparation of acrylonitrile, comprising bringing, at an elevated temperature, a reaction feed containing propylene, molecular oxygen and ammonia, each in gas phase, into contact with a catalyst consisting of an oxide composition of the empirical formula:

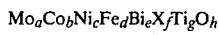

$$Mo_aCo_bNi_cFe_dBi_eX_fTi_gO_h$$

wherein X represents at least one atom of an element selected from vanadium and tellurium, the subscripts a, b, c, d, e, f and g respectively denote the numbers of the respective atoms of the elements, the ratio a:b:c:d:e:f:g being in the range of 10:0 to 10:0 to 10:1 to 7:0.08 to 1.1:0.01 to 1:1 to 15, and the ratio of a to the sum of b and c being in a range of 10:3 to 10, and; the subscript h represents the number of oxygen atoms which satisfies the average valency of the elements, the ratio a:h being in a range of 10:36.7 to 84.1.

2. A process as claimed in claim 1, wherein the ratio a:b:c:d:e:f:g is in a range of 10:1 to 7:0 to 7:1.5 to 7:0.1 to 0.5:0.05 to 0.5:2 to 10 and the ratio of a to the sum of b and c is in a range of 10:4 to 9.

3. A process as claimed in claim 1, wherein X in the empirical formula represents tellurium.

4. A process as claimed in claim 1, wherein said catalyst is prepared by providing an aqueous mixture containing a molybdenum-containing compound, a cobalt-containing compound, a nickel-containing compound, an iron-containing compound, a bismuth-containing compound, at least one member selected from vanadium- and tellurium-containing compounds and a titanium-containing compound; converting said aqueous mixture into a dried solid mixture, and; calcining said dried solid mixture at a temperature of from 500° to 700° C.

5. A process as claimed in claim 4, wherein said calcining operation is carried out for from 0.5 to 20 hours.

6. A process as claimed in claim 1, wherein said catalyst in borne on a carrier having no catalytic activity consisting of at least one member selected from silica, alumina, silica-alumina, zirconia, titania, diatomaceous earth and silicates.

7. A process as claimed in claim 6, wherein the amount of said carrier is in a range of from 0.05 to 3 g per g of said catalyst.

8. A process as claimed in claim 6, wherein said catalyst borne on said carrier is in a size of from 30 to 100 microns.

9. A process as claimed in claim 1, wherein said reaction feed contains an inert diluent gas, in addition to said propylene, molecular oxygen and ammonia.

10. A process as claimed in claim 1, wherein said contact of said reaction feed with said catalyst is carried out at a temperature of from 330° to 470° C.

11. A process as claimed in claim 1, wherein said contact is carried out for 0.2 to 7 seconds.

12. A process as claimed in claim 1, wherein the source of said propylene to be present in said reaction feed is free from n-butylene and acetylene.

13. A process as claimed in claim 1, wherein the source of said molecular oxygen to be present in said reaction feed is either pure oxygen gas or air.

14. A process as claimed in claim 1, wherein the amount of said molecular oxygen in said reaction feed is in a range of from 1 to 4 moles per mole of said propylene.

15. A process as claimed in claim 1, wherein the amount of said ammonia in said reaction feed is in a range of from 0.5 to 2 moles per mole of said propylene.

16. A process as claimed in claim 1, wherein the concentration of said propylene in said reaction feed is in a range of from 1 to 20% by volume.

* * * * *